United States Patent [19]

Sneider

[11] 4,329,990

[45] May 18, 1982

[54] EXPANDING SWAB APPLICATOR

[76] Inventor: Vincent R. Sneider, 3422 Hallcrest Dr., NE., Atlanta, Ga. 30319

[21] Appl. No.: 176,105

[22] Filed: Aug. 7, 1980

[51] Int. Cl.³ .............................................. A61M 3/00
[52] U.S. Cl. .................................. 128/239; 128/243; 128/269; 401/196
[58] Field of Search ............... 128/756, 759, 239, 243, 128/246, 269, 345; 401/196

[56] References Cited

U.S. PATENT DOCUMENTS

| | | |
|---|---|---|
| 2,490,168 | 12/1949 | Strauss . |
| 3,054,403 | 9/1962 | Baker . |
| 3,086,527 | 4/1963 | Forrest . |
| 3,204,635 | 9/1965 | Voss et al. . |
| 3,228,398 | 1/1966 | Leonard et al. . |
| 3,324,855 | 6/1967 | Heimlich ............................. 128/269 |
| 3,495,917 | 2/1970 | Truhan . |
| 3,512,518 | 5/1970 | Mishkin et al. ..................... 128/756 |
| 3,512,526 | 5/1970 | Fielding . |
| 3,519,364 | 7/1970 | Truhan . |
| 3,645,263 | 2/1972 | Bates . |
| 3,709,224 | 1/1973 | Fielding . |
| 3,731,682 | 5/1973 | Fielding . |
| 3,818,911 | 6/1974 | Fournier . |
| 3,830,236 | 8/1974 | Hanke . |

3,938,898  2/1976  Reitknecht .

*Primary Examiner*—C. Fred Rosenbaum
*Attorney, Agent, or Firm*—Ralph R. Roberts

[57] ABSTRACT

A swab applicator is disclosed for use as a vaginal cleansing instrument, or the like. The applicator includes an elongated, generally hollow tubular nozzle, with a compressed swab body of soft, porous and absorbent material generally at the distal end of the nozzle and in fluid communication therewith. The swab body is highly expandable when wetted, and retaining means in the form of a plurality of spaced ribs form a cage surrounding the swab body to hold the body in position on the distal end of the nozzle and permit the swab body to expand through slots between the ribs when the swab body is wetted. The swab body has fluid passages therethrough to enhance its wetting by liquid dispensed through the nozzle. The nozzle has teeth on the interior thereof for cutting troughs, during assembly, into the exterior of the swab body beneath the spaced ribs and along which liquid can travel to further enhance wetting of the swab body by liquid dispensed through the nozzle. Further fluid passages are formed through the teeth to lubricate the exterior of the applicator and the interior of the vaginal cavity.

23 Claims, 7 Drawing Figures

EXPANDING SWAB APPLICATOR

BACKGROUND OF THE INVENTION

This invention relates to a swab applicator for use as a vaginal cleansing instrument, or the like.

Heretofore, a wide variety of swab applicators, vaginal cleansing instruments, surgical sponge sticks, douche tip sponge sheaths, and the like have been provided for use as sanitary or surgical apparatus. In most instances, a sponge or an absorbent body is disposed on the tip of an applicator holder, nozzle or dispenser. In many instances, the swab is maintained in fluid communication with apertures in the tip of the holder, the holder itself often forming a nozzle for attachment to a fluid dispenser such as a syringe.

One of the problems with swab applicators of the character described is that the swab itself often becomes dislodged from the applicator holder and/or "floats" relative to the applicator holder and does not fulfill its intended swabbing function. To solve this problem, certain sponge type materials are used, but the sponge materials are not very absorbent and are capable of only limited expansion. There is a need for providing a swab applicator which utilizes a compressed swab body of soft porous and absorbent material which is highly expandable when wetted, but which is free of the problems described.

Another problem with swab applicators of the character described, particularly with applicators which are used as vaginal cleansing instruments, or the like, is that the applicator holder or nozzle is relatively rigid. Such rigid applicators not only are uncomfortable to the user, but they actually can cause injury to the vaginal cavity, or the like.

The present invention relates to a swab applicator of the character described which is directed to solving these and other related problems.

SUMMARY OF THE INVENTION

An object, therefor, of the present invention is to provide a new and improved swab applicator for use as a vaginal cleansing instrument, or the like.

In the exemplary embodiment of the invention, the swab applicator includes a compressed swab body of soft, porous and absorbent material which is highly expandable when wetted. An elongated applicator holder is provided for the swab body, with retaining means on the distal end thereof and partially surrounding the swab body to hold the swab body in position and permit the body to expand through the retaining means when wetted. In this manner, only the soft, porous and absorbent material comes into contact with the vaginal cavity.

The retaining means generally is in the form of a cage defined by a plurality of generally equally spaced elonaged ribs extending generally in the longitudinal direction of the applicator holder. The ribs define a plurality of slots therebetween and through which the swab body can expand when wetted. Preferably, the ribs are molded integrally with the applicator holder and converge into a smooth rounded end portion to prevent injury to the vaginal cavity.

An important feature of the invention is that the ribs are sufficiently resilient to permit bending thereof, along with the swab body, and thereby prevent injury to the vaginal cavity.

In the disclosed form of the invention, the applicator holder is in the form of an elongated, generally hollow tubular nozzle, including means opposite the swab body for attaching the nozzle in fluid communication with an appropriate liquid dispenser, such as a syringe or the like.

The swab body has fluid passages therethrough to enhance its wetting by liquid dispensed through the nozzle. The nozzle has teeth on the interior thereof for cutting troughs, during assembly, into the exterior of the swab body beneath the spaced ribs and along which liquid can travel to further enhance wetting of the swab body by liquid dispensed through the nozzle. Further fluid passages are formed through the teeth to lubricate the exterior of the applicator and the interior of the vaginal cavity.

In another form of the invention, the swab body is shaped in the form of a sheath, and the retaining means on the distal end of the applicator holder extends into the sheath to retain the swab onto the end of the holder and in fluid communication therewith. Again, the retaining means is sufficiently resilient to permit bending thereof, along with the swab sheath, and thereby prevent injury to the vaginal cavity or the like.

Thus, it can be seen that a new and improved swab applicator has been provided which solves the problems heretofore enumerated. It should be understood that although the swab applicator of the present invention is shown in the form of an appropriate vaginal cleansing instrument, the concepts of the invention are equally applicable for other surgical and sanitary applications.

DETAILED DESCRIPTION OF THE INVENTION

Figure 1:
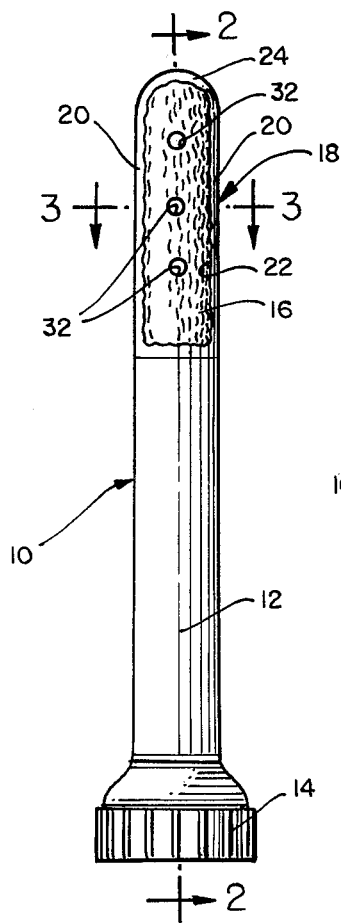
FIG. 1 is an elevational view of the swab applicator of the present invention, incorporated in a nozzle attachment.
Figures 2, 2A:
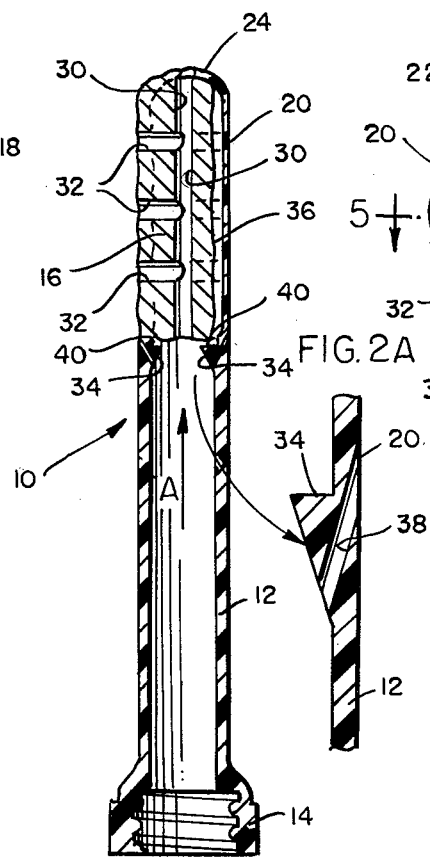
FIG. 2 is a vertical sectional view taken generally along the line 2—2 of FIG. 1.
FIG. 2A is an enlarged, fragmented sectional view showing one of the teeth molded integrally with the interior of the nozzle.
Figures 3, 5:
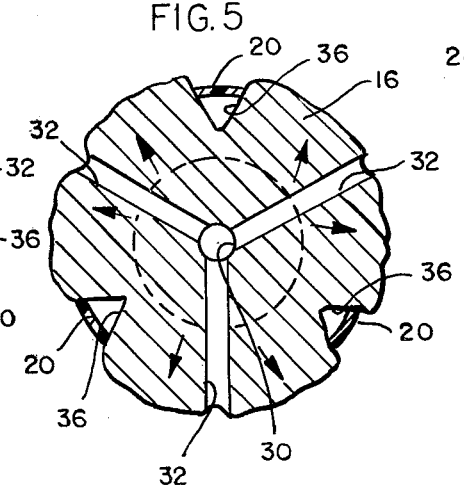
FIG. 3 is a horizontal sectional view taken generally along the line 3—3 of FIG. 1.
FIG. 5 is a horizontal sectional view taken generally along the line 5—5 of FIG. 4.

Referring to the drawings in greater detail, and first to FIGS. 1-3, a swab applicator, generally designated 10, is shown for use as a vaginal cleansing instrument, or the like. Of course, it is to be understood that the swab applicator, incorporating the concepts of the present invention hereinafter described, is equally useful for a wide variety of surgical, hygienic, and like applications.

Swab applicator 10 includes an applicator holder in the form of an elongated, generally tubular nozzle 12. Nozzle 12 has an internally threaded base 14 for attaching the nozzle in fluid communication with an appropriate liquid dispenser, such as a syringe or the like. Of course, it is to be understood that an appropriate handle of other applicator holder is contemplated for use with the novel swab tip of the present invention as described hereinafter.

Swab applicator 10 includes a compressed swab body 16 of soft, porous and absorbent material which is highly expandable when wetted, such as known tampon materials.

Retaining means, generally designated 18 (FIG. 1), is provided on the distal end of nozzle 12 and partially surrounds swab body 16 to hold the swab body in position and permit the swab body to expand through the retaining means when wetted. More particularly, the retaining means generally is in the form of a cage defined by a plurality of generally equally spaced elongated ribs 20 extending generally in the longitudinal direction of the nozzle. Ribs 20 define a plurality of slots 22 therebetween and through which swab body 16 can expand when wetted. The ribs converge into a smooth rounded end portion 24 to prevent injury to the vaginal cavity or the like.

Nozzle 12 and retaining means 18 (i.e. ribs 20 and end portion 24) can be molded integrally as a self contained unit of suitable plastic material or the like.

An important feature of the present invention is that the ribs 20 are sufficiently flexible to permit bending thereof, along with swab body 16, during use and thereby prevent injury to the vaginal cavity or the like. At the same time, the ribs provide a containing structure or cage to prevent the swab body from becoming dislodged from the applicator holder and prevent the swab body from unnecessarily "floating" during its intended use.

Various features are provided to enhance the wetting of swab body 16 by liquid dispensed through nozzle 12. More particularly, the swab body has a central, axial fluid passage 30 communicating with the interior of the nozzle, and a plurality of radial fluid passages 32 communicating with axial passages 30. Liquid thus can be dispensed through the interior of the nozzle and into passages 30 and 32 which create a larger surface area of the swab body for absorbing the liquid. Initially, a portion of the liquid can pass through the passages to lubricate the walls of the vaginal cavity during initial insertion of the applicator.

A further novel feature of the invention is the provision of angled teeth 34 molded integrally with the interior of nozzle 12 in axial alignment with ribs 20. These teeth are effective to cut troughs 36 (see FIGS. 3 and 4), during assembly, into the exterior of swab body 16 beneath the spaced ribs 20. Troughs 36 and ribs 20 form further enclosed fluid passages along which liquid can travel to further enhance wetting of swab body 16 by liquid dispensed through the nozzle. During assembly, the swab body is pushed into position from the open end 14 of the nozzle in the direction of arrow A, FIG. 2. As the swab body is forced past teeth 34, the teeth are effective to cut troughs 36 into the exterior of the swab body.

The teeth 34 themselves are formed with bores 38 converging outwardly at an angle as shown in FIG. 2. These bores provide further fluid passages for liquid dispensed through nozzle 12, for lubricating the exterior of the applicator and the interior of the vaginal cavity to facilitate insertion of the applicator and further enhance wetting of swab body 16 from the exterior thereof. The teeth also have flat forwardly facing stop surfaces 40, which will block any reverse movement of the swab body.

Figure 4:
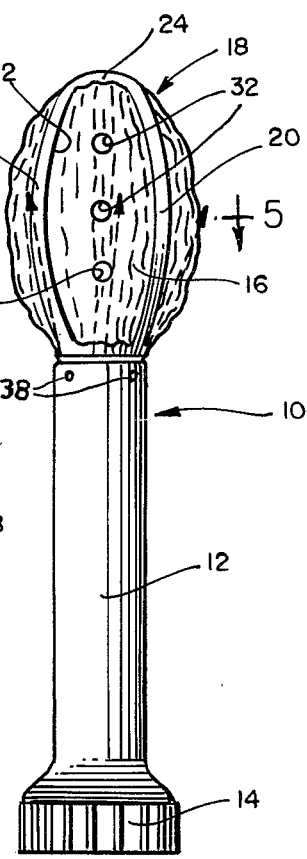
FIG. 4 is an elevational view of the swab applicator of FIG. 1, with the swab body thereof in wetted, expanded condition.

Referring to FIGS. 4 and 5, the condition of swab body 16 is shown after having been wetted by an appropriate liquid, such as water. As seen in FIG. 4, the resiliency of ribs 20 enable the swab body to fully expand when wetted, while at the same time retaining the swab body in proper position on the distal end of nozzle 12. As seen in FIG. 5, swab body 16, in its wetted and expanded condition, extends radially outwardly beyond the bounds of ribs 20 for contact with the vaginal cavity and, in fact, the ribs become sufficiently recessed within the swab body so that a thorough cleansing of the cavity can be performed without any danger of the ribs themselves causing injury to the cavity.

In use, the swab applicator 10 of the present invention is packaged with swab body 16 in its compressed condition as shown in FIGS. 1-3. The swab body can be wetted by simply submerging the body in an appropriate liquid, such as water, until the body is fully expanded through the slots 22, between ribs 20. Of course, other appropriate liquids may be employed for surgical or hygienic purposes. To this end, the material of which the swab body is fabricated should be uneffected by human body fluids, antiseptics, anesthetics, and other desirable fluids. If swab applicator 10 is employed as a fluid nozzle, as shown in FIGS. 1, 2 and 4, the swab body can be wetted by liquid from an appropriate fluid dispenser or syringe through nozzle 12 and into the swab body, with the nozzle attached to the dispenser by appropriate means such as internally threaded base 14.

Figure 6:
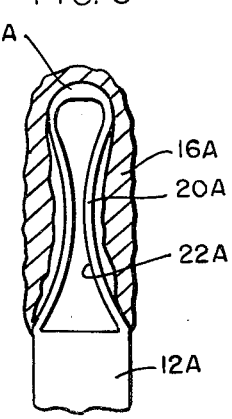
FIG. 6 is a fragmented view of an alternate form of swab applicator.

Referring to FIG. 6, a modified form of invention is shown with an internal, flexible retaining means for a swab body. More particularly, a nozzle 12A has a plurality of flexible ribs 20A molded integrally therewith, with the ribs converging into a relatively rigid head portion 24A. A swab body 16A is provided in the form of a sheath for positioning over the retaining means formed by ribs 20A, 24A. The same type of compressed soft, porous and absorbent material for swab body 16A is utilized as described above. Ribs 20A define slots 22A therebetween and through which liquid from nozzle 12A can be discharged for wetting and expanding the sheath-type swab body 16A. When the body expands, after wetting, ribs 20A tend to bend inwardly, as shown, and the relatively rigid head portion 24A is effective to hold the swab sheath in position, while at the same time permitting the body to bend with ribs 20A and thereby prevent injury to the vaginal cavity or the like.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. A swab applicator for use as a vaginal cleansing instrument or the like, an including:
   (a) an elongated, generally hollow tubular nozzle having an entering and distal end including means on said elongated nozzle and opposite the entering end for attaching the nozzle so as to be in fluid communication with an appropriate liquid dispenser;
   (b) a swab body of absorbent, expandable material disposed generally at the distal end of said nozzle and in fluid communication therewith, and
   (c) a cage providing retaining means for the swab body, said cage disposed within said distal end of the nozzle with the cage having a plurality of generally equally spaced elongated ribs which extend generally in the longitudinal direction of the nozzle and defining a plurality of slots therebetween and through which said swab body can expand when wetted and with the ends of the ribs brought into a smooth rounded end portion at the distal entering end, this rounded end adapted to prevent injury to the vaginal cavity or the like.

2. The swab applicator of claim 1 wherein said ribs are sufficiently resilient to permit bending thereof, along with said swab body, and thereby prevent injury to the vaginal cavity or the like.

3. The swab applicator of claim 1 wherein said ribs are molded integrally with said nozzle.

4. The swab applicator of claim 1, further including troughs formed along the exterior of said swab body beneath said ribs to provide fluid passages to enhance wetting the swab body by liquid dispensed through said nozzle.

5. The swab applicator of claim 4 wherein said nozzle has an axial bore through which said swab body is inserted during assembly, and further including teeth formed within said bore for cutting said troughs into the exterior of said swab body.

6. The swab applicator of claim 5, further including fluid passage means formed through said teeth for lubricating the exterior of said applicator by liquid dispensed through said nozzle.

7. The swab applicator of claim 1, further including fluid passage means extending through said swab body and outwardly between said ribs to enhance wetting of the swab body by liquid dispensed through said nozzle.

8. The swab applicator of claim 1 wherein said ribs are sufficiently resilient to permit bending thereof, along with said swab body, and thereby prevent injury to the vaginal cavity or the like.

9. The swab applicator of claim 1 wherein said cage is molded integrally with said nozzle.

10. The swab applicator of claim 1, further including fluid passage means extending through said swab body in communication with the interior of said nozzle.

11. The swab applicator of claim 1, further including fluid passage means through said nozzle axially inwardly of said swab body for lubricating the exterior of said applicator by liquid dispensed through said nozzle.

12. A swab applicator for use as a vaginal cleansing instrument or the like and including:
(a) a compressed swab body of soft, porous and absorbent material which is highly expandable when wetted, and
(b) an applicator holder for said swab body including a cage providing retaining means for said swab body, said cage having a plurality of generally equally spaced elongated ribs providing in slots therebetween aperture means through which fluids may pass and through which the swab body can expand when said swab body is wetted.

13. The swab applicator of claim 12, further including troughs formed along the exterior of said swab body beneath said ribs to provide fluid passages to enhance wetting the swab body by liquid dispensed through said nozzle.

14. The swab applicator of claim 13 wherein said nozzle has an axial bore through which said swab body is inserted during assembly, and further including teeth formed within said bore for cutting said troughs into the exterior of said swab body.

15. The swab applicator of claim 14, further including fluid passage means formed through said teeth for lubricating the exterior of said applicator by liquid dispensed through said nozzle.

16. The swab applicator of claim 12 wherein said ribs converge into a smooth rounded end portion to prevent injury to the vaginal cavity or the like.

17. The swab applicator of claim 12 wherein said ribs are sufficiently resilient to permit bending thereof, along with said swab body, and thereby prevent injury to the vaginal cavity or the like.

18. The swab applicator of claim 12 wherein said ribs are molded integrally with said holder.

19. The swab applicator of claim 12 wherein said ribs are sufficiently resilient to permit bending thereof, along with said swab body, and thereby prevent injury to the vaginal cavity or the like.

20. A swab applicator for use as a vaginal cleansing instrument or the like, and including:
(a) an elongated generally hollow tubular nozzle having an entering and distal end including means on said elongated nozzle and opposite the entering end for attaching the nozzle so as to be in fluid communication with an appropriate liquid dispenser;
(b) a swab body of absorbent, expandable material disposed generally at the distal end of said nozzle and in fluid communication therewith, and
(c) a cage integrally molded to and with said nozzle, said cage providing the distal end of the applicator and with said cage having a plurality of generally equally spaced elongated ribs which extend generally in the longitudinal direction of the nozzle and with said ribs defining a plurality of slots therebetween and through which said swab body can expand when wetted, said ribs being sufficiently resilient to permit bending thereof, along with said swab body, and with the ends of the ribs brought into a smooth rounded end portion at the distal entering end, this rounded end and resilient ribs adapted to prevent injury to the vaginal cavity or the like.

21. The swab applicator of claim 20, further including troughs formed along the exterior of said swab body beneath said ribs to provide fluid passages to enhance wetting the swab body by liquid dispensed through said nozzle.

22. The swab applicator of claim 21 wherein said nozzle has an axial bore through which said swab body is inserted during assembly, and further including teeth formed within said bore for cutting said troughs into the exterior of said swab body.

23. The swab applicator of claim 22, further including fluid passage means formed through said teeth for lubricating the exterior of said applicator by liquid dispensed through said nozzle.

* * * * *